Figure 1:
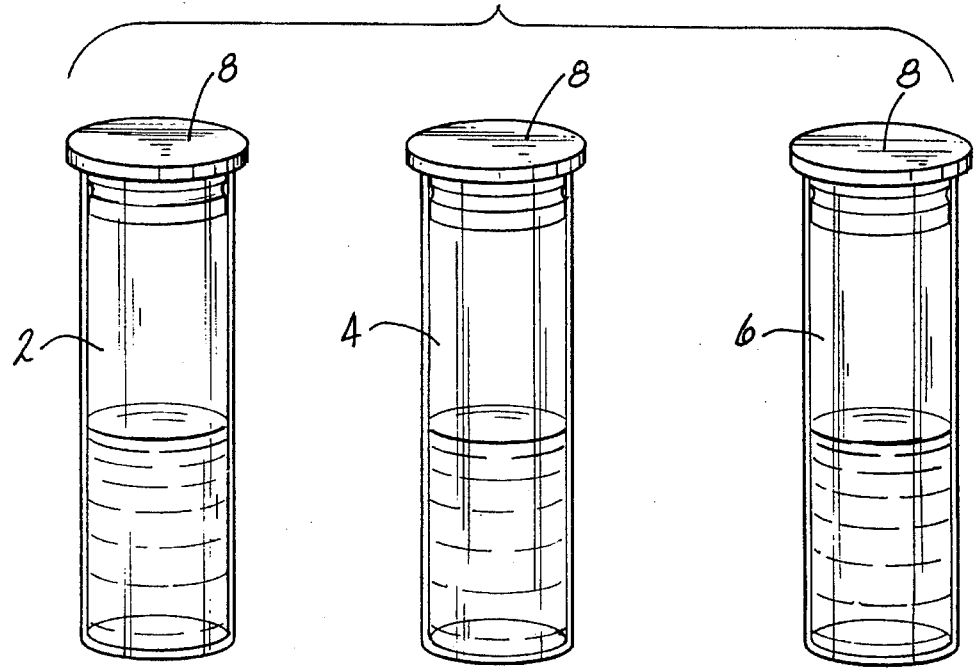

United States Patent [19]

Levine et al.

[11] Patent Number: 5,480,778
[45] Date of Patent: Jan. 2, 1996

[54] DETERMINATION OF LYMPHOCYTE REACTIVITY TO SPECIFIC ANTIGENS IN BLOOD

[76] Inventors: Robert A. Levine, 31 Pilgrim La., Guilford, Conn. 06437; Stephen C. Wardlaw, 191 N. Cove Rd., Old Saybrook, Conn. 06475

[21] Appl. No.: 6,766

[22] Filed: Jan. 21, 1993

Related U.S. Application Data

[60] Continuation of Ser. No. 785,099, Oct. 31, 1991, abandoned, which is a division of Ser. No. 340,248, Apr. 19, 1989, abandoned.

[51] Int. Cl.⁶ ..................................................... G01N 33/53
[52] U.S. Cl. ....................... 435/7.24; 422/68.1; 435/975
[58] Field of Search ............................... 435/4, 7.21, 967, 435/7.24, 975; 436/808, 513; 422/68.1

[56] References Cited

U.S. PATENT DOCUMENTS

| | | |
|---|---|---|
| 4,077,396 | 3/1978 | Wardlaw et al. |
| 4,436,824 | 3/1984 | Bishop ..................................... 436/514 |
| 4,727,020 | 2/1988 | Recktenwald ............................... 435/6 |
| 4,788,137 | 11/1988 | Reinnerz et al. ....................... 435/7.24 |
| 5,320,947 | 6/1994 | Cheever et al. ........................ 435/7.23 |

FOREIGN PATENT DOCUMENTS

| | | |
|---|---|---|
| 0227335 | 7/1985 | European Pat. Off. . |
| 1649445 | 5/1991 | U.S.S.R. . |
| 1691751 | 11/1991 | U.S.S.R. . |

OTHER PUBLICATIONS

Dattwyler et al., N. Engl. J. Med. (1988) 319:1441–6.
Chatila et al., N. Engl. J. Med. (1989) 320:696.
Levine et al., American Scientist 76 (1988).

*Primary Examiner*—David Saunders
*Attorney, Agent, or Firm*—William W. Jones

[57] ABSTRACT

A patient's blood sample is incubated with an antigen and tested for lymphocyte response, ie. an activation of lymphocytes and/or a conversion of lymphocytes to lymphoblasts, which indicates prior exposure of the patient to the antigen. A positive response indicates the presence of prior exposure to prior diseases or clinical conditions such as parasitic diseases, tuberculosis, salmonellosis, gonorrhea, fungal infections, rickettsial infections, Lyme disease or allergens. Whole blood from the patient is incubated with the antigen of the disease or condition for which the patient is being tested. After a suitable time, a fluorescent dye or colorant is added which has an affinity for a discriminant characteristic of the activated lymphocytes or lymphoblasts, such as: intracellular calcium; surface activation antigens such as transferrin receptor; HLA-Dr; Leu-23; and the like. The incubated blood is then drawn into a transparent tube containing a float which concentrates the buffy coat constituent layers upon centrifugation of the blood sample. The concentrated lymphocyte layer is then examined for fluorescence or coloration which is indicative of the presence of the activated lymphocytes or lymphoblasts, and their concentration. The fluorescence or coloration can be qualified and/or quantified by a reader instrument.

1 Claim, 1 Drawing Sheet

U.S. Patent　　　　　　　Jan. 2, 1996　　　　　　　5,480,778

DETERMINATION OF LYMPHOCYTE REACTIVITY TO SPECIFIC ANTIGENS IN BLOOD

This is a continuation of application U.S. Ser. No. 07/785,099, filed Oct. 30, 1991, now abandoned, which in turn was a division of U.S. Ser. No. 07/340,248, filed Apr. 19, 1989, now abandoned.

This invention relates to a procedure for determining whether a patient has been previously exposed to certain antigens, and more particularly, to antigens indicative of diseases, infections, allergies or the like maladies.

When diagnosing patients for possible illness or the like, the physician will typically perform blood tests to determine the presence or absence of agents in the blood which are indicative of prior exposure to various diseases or other maladies. Traditional tests to determine a patient's previous exposure to antigens, generally infectious agents, have usually relied upon tests for the presence or absence of a circulating humoral antibody directed against the proposed antigen. An example of such tests include blood tests to detect: immunity to Rubella (German measles); and a multitude of other viral and bacterial antigens. The means of detecting the antibody are many and include: latex agglutination in which the agglutination or lack of agglutination of antigen-coated latex particles is observed; enzyme linked immuno substrate assay (ELISA) in which the development of a color is observed either visually or spectrophotometrically; radioimmunoassay in which the measurement of radioactivity is measured; liposome technology in which the presence and intensity (or absence) of a color or fluorescent dye contained in the liposomes is detected; radio immuno sorbant assay (RAST) in which the measurement of radioactivity adherent to a solid substrate is measured; and indirect immunofluorescence in which the immobilized antigen to which the antibody to be detected is allowed to react with the specimen being tested, the antigen being washed to remove non-specifically adherent antibodies, and a fluorescently tagged antibody directed against the class of the antibody being tested for is applied, and the presence or absence of fluorescence is determined; as well as other methodologies. Antibodies, when present, can be titered, and their immune globulin class (of most interest are: IgM, signifying acute exposure; IgG, signifying past exposure; and IgE, signifying an allergic state) can be determined thereby determining the subject's previous exposure to the given antigen. All of the above tests are measurements of the function of a group of lymphocytes called B-lymphocytes. In cases, or disease processes, where little or no antibody response is made, the above tests will fail to determine the subject's previous exposure.

Many diseases and clinical states, however, may not result in detectable humoral antibodies, ie, a B-lymphocyte response, but do in fact produce cellular immunity, ie, a T-lymphocyte response. Examples of such diseases and clinical conditions where the T-lymphocyte response predominates include many parasitic diseases, tuberculosis, salmonellosis, gonorrhea, fungal infections, rickettsial infections, and Lyme disease. As recently reported by Dattwyler et al (New England Journal; of Medicine, Vol. 319, at 1441, 1988) a significant proportion of patients, including some who have received some antibiotic therapy early in the course of the disease, do not produce detectable antibodies to the Lyme disease spirochete, but do have a measurable T-lymphocyte response.

There are two general ways for determining whether a T-lymphocyte response has taken place in the blood due to prior exposure to diseases, infectious agents, or the like. The first procedure relies on the presence of morphologic cell changes which arise from prior exposure. Previously exposed T-lymphocytes will assume blast-like characteristics when re-exposed to the particular antigens. For example, the T-lymphocytes will develop a larger than normal nucleus and an abundant basophilic cytoplasm. Biochemical changes indicative of activation will also occur, such as: increased turnover of membrane phospholipids; increased synthesis of RNA and proteins; changes in intra-cellular $Ca^{++}$ concentration; expression of surface receptor for T-cell growth factor interleukin-2; and increase in the incorporation 3H-thymidine, as well as other events summarized in a recent article by Chatila, T. et al (New England Medical Journal, Vol. 320, page 696, 1989).

The method most used in the past to assay T-lymphoblasts, and the one used by Dattwyler et al in their study of Lyme disease, to detect the presence or absence of a specific T-lymphocyte response to a given antigen is the tritiated thymidine uptake assay (3H-thymidine uptake assay). This assay is cumbersome, requires the use of radioactive isotopes, and requires the isolation of relatively pure populations of lymphocytes, and also takes several days to complete.

This invention relates to a simple technique for detecting the presence or absence of previously exposed T-lymphocytes in a patient's blood. The patient's whole blood is incubated with the antigen for the suspected malady being diagnosed, which antigen is dispersed in a suitable pH-regulated medium, such as a buffered saline solution, for example. This incubation will cause previously exposed lymphocytes to become activated and eventually to assume the blast morphology, ie, to become lymphoblasts. After a suitable incubation period, a fluorescent dye, such as the acetomethylester of the calcium-sensitive dye fura-2, or other colorant having an affinity for activated lymphocytes or lymphoblasts is added to the blood sample. The dye can obtain its attraction to the activated lymphocytes or resultant lymphoblasts through chemical means, ie, by being combinable with the excess calcium ions, or by other means, such as by being tagged with a fluorescently-tagged antibody specific to the transferrin, Leu-23, the surface receptor for T-cell growth factor interleukin-2, or the like. The addition of the dye, colorant, or fluorescently tagged antibody will differentially highlight any responding lymphocytes or lymphoblasts in the blood sample. It should be noted that the highlighting additive may bind to responding lymphocytes, either before or after they have become true iymphoblasts. Pre-sensitized lymphocytes may therefore exhibit the characteristics which attract the additive before complete morphological changes occur. The treated blood is then centrifuged in a transparent tube having a float therein which will concentrate all of the lymphocytes, including any lymphoblasts, in a small area in the tube. The latter cell concentrating technique is disclosed in U.S. Pat. No. 4,027,660 granted Jun. 7, 1977 to Stephen Clark Wardlaw et al. The tube can be a capillary tube, or a pre-evacuated larger tube. After the cell concentration has been performed, the lymphocyte layer is examined to detect coloration or flourescence levels which are indicative of the presence of lymphoblasts in the lymphocyte layer. The detection of such color or fluorescence characteristics can be performed with an instrument such as those disclosed in U.S. Pat. No. 4,156,570 granted May, 1978 and U.S. Pat. No. 4,558,947, granted December, 1985 both to Stephen C. Wardlaw.

It is therefore an object of this invention to provide an improved precedure and paraphenalia for diagnosing prior patient exposure to a suspect antigen which sensitizes lymphocytes in the patient's blood.

It is a further object of this invention to provide a procedure of the character described wherein an optically detectable indicator is added to the blood sample to optically highlight responding lymphocytes in the blood sample.

It is an additional object of this invention to provide a procedure of the character described wherein the sensitized lymphocytes are T-lymphocytes.

It is another object of this invention to provide a procedure of the character described wherein the blood sample is centrifuged in a transparent tube to concentrate the lymphocytes in a band which is then optically analysed for indication of highlighting.

Figure 2:
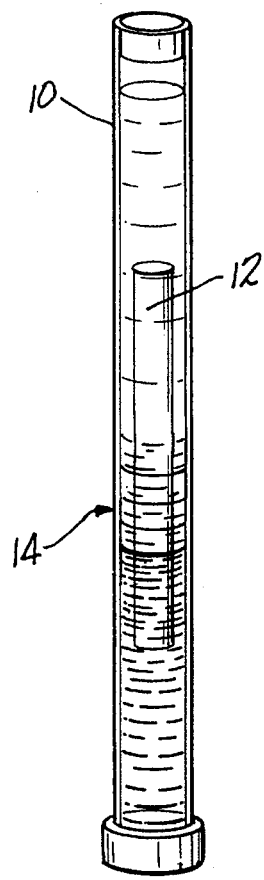

These and other objects and advantages will become more readily apparent from the following detailed description of a preferred embodiment of the invention when considered in connection with the accompanying drawings, in which:

FIG. 1 is a perspective view of three sample tubes used in a kit for performing the procedure of the invention; and FIG. 2 is a perspective view of a centrifuge tube showing layering out of the blood cells for examination for optical highlighting.

The invention admits to the inclusion of negative and positive controls. A negative control is used to determine that the T-lymphcytes do not respond to non-specific stimuli. The positive control is used to determine whether the patient's lymphocytes are capable of responding to antigens either singly or in combination that the physician knows that the patient has been exposed to in the past such as tetanus toxoid, diphtheria toxoid, monslia, or chemicals known to activate lymphocytes, such as phytohemaggluttimins, aluminum fluoride, or the like.

The patient's blood can be placed in three separate reagent wells, or containers, a negative test control container 2, a sampling container 4, and a positive test control container 6, each of which has a stoppered closure 8 through which the blood may be transferred. The stain can be added separately or may be precoated into the interior of the three containers.

The negative test container 2 has the antigen medium in it, but no antigens. The blood is added to the antigen medium, incubated therein, the same as with the test sample, and the colorant or fluorescent is added. The blood sample is then centrifuged in a centrifuge tube 10 containing a plastic float 12 which restricts the space available for the lymphocyte/monocyte cell band 14. This band is then examined for evidence of highlighting. If any is observed, the veracity of a like result in the test sample will be open to question, since lymphocyte activation can spontaneously occur in a blood sample. If no color change is seen, then the veracity of the sample results are confirmed, ie, it is confirmed that no spontaneous lymphoblasts are present in the blood sample.

The positive test container 6 is used to mix the blood sample with either an antigen (as described above) from infectious agents, which are known to activate lymphocytes in the vast majority of normal patients. The positive incubation mixture is then centrifuged as shown in FIG. 2 with a colorant or fluorescent that has an affinity for the yeast-induced lymphoblasts which will form in the incubated blood sample. The presence or absence of highlighted lymphoblasts in the cell band 14 will then be noted. If they are present, then the susceptability of the patient's blood to the test is confirmed. If none is noted, then the physician can confirm that the patient is not susceptable to the test, and a protocol may be used to determine the reason for the lack of a positive response to the disease antigens being tested for, and the negative response to the tested antigen will not be considered indicative of lack of previous exposure and sensitization to the same.

The utility of the test on the patient can thus be confirmed by the patient's positive response to the positive control and negative response to the negative control.

This invention differs from previous procedure in the following ways:

1. It, unlike the individual cell counters which determine the fluorescent signal from each individual call, utilizes the integrated fluorescence of the entire population of packed lymphocytes (several hundred thousands contained in the lymphocyte/monocyte band of a centrifuged capillary tube containing 110 micro liters of blood);

2. It does not require prior purification and isolation of the lymphocytes and may therefore be performed on whole blood (anticoagulated);

3. It does not require the use of any radioactive isotopes; and

4. The use of an integral negative and positive control together with a predetermined amount of antigen in a combined test-pack, together with software interpreting the result, permit its easy use by non-research trained personnel.

The potential utility of an easily performed test of T-lymphocyte response to an antigen cannot be over-emphasized. In addition to possible aiding in the diagnosis of the diseases listed previously, the invention's testing methodology may be useful in the following conditions: diagnosing the cause of delayed hypersensitivity reactions such as eczema or contact dermatitis; diagnosing certain viral infections during the window period prior to measurable antibody response; following the course of autoimmune disease; and in the diagnosis of the presence of tumor antigens or as a measure of anti-tumor immunity.

The test can also be performed with a panel of antigens for example, antigens from several species of malaria. If a positive reaction is seen, then individual species tests can be performed to identify the species of malaria involved. Panel testing of allergens can also be performed with subsequent specific tests.

The invention has been described in conjunction with human patients, but it could also be used on animals.

Since many changes and variations in the disclosed embodiment of the invention may be made without departing from the inventive concept, it is not intended to limit the invention otherwise than as required by the appended claims.

What is claimed is:

1. Paraphernalia for determining a patient's prior exposure to a suspect antigen to which lymphocytes in whole blood may have become sensitized, said paraphernalia comprising:

a) three transparent stoppered incubation containers for receiving whole blood samples, said containers including:

i) a first container containing said suspect antigen in a pH controlled medium;

ii) a second container containing said pH controlled medium, said second container being devoid of said suspect antigen; and iii) a third container containing an antigen to which prior patient exposure has been shown; and b) a colorant having an affinity for activated lymphocytes or lymphoblasts which result from incubation of a whole blood sample in said containers.

* * * * *